United States Patent
Asmussen et al.

(10) Patent No.: US 8,262,604 B2
(45) Date of Patent: Sep. 11, 2012

(54) SINGLE-USE INJECTOR WITH AT LEAST ONE DRAW HOOK

(75) Inventors: Bodo Asmussen, Bendorf (DE); Hans-Rainer Hoffmann, Neuwied (DE); Rudolf Matusch, Marburg (DE); Uwe Wortmann, Marburg (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 0 days.

(21) Appl. No.: 12/455,964

(22) Filed: Jun. 10, 2009

(65) Prior Publication Data

US 2009/0254036 A1 Oct. 8, 2009

Related U.S. Application Data

(63) Continuation-in-part of application No. PCT/EP2008/000102, filed on Jan. 9, 2008.

(30) Foreign Application Priority Data

Jan. 27, 2007 (DE) .......................... 10 2007 004 211

(51) Int. Cl.
  *A61M 5/30* (2006.01)
(52) U.S. Cl. ............................................ 604/68; 604/72
(58) Field of Classification Search .............. 604/68–72, 604/135–137, 34; 64/68–72, 135
See application file for complete search history.

(56) References Cited

U.S. PATENT DOCUMENTS

| 4,316,463 A | * | 2/1982 | Schmitz et al. | 604/135 |
| 4,553,962 A | | 11/1985 | Brunet | |
| 4,565,543 A | * | 1/1986 | Bekkering et al. | 604/135 |
| 4,968,302 A | * | 11/1990 | Schluter et al. | 604/135 |
| 5,334,144 A | * | 8/1994 | Alchas et al. | 604/68 |
| 2005/0124940 A1 | | 6/2005 | Martin et al. | |
| 2005/0203466 A1 | | 9/2005 | Hommann et al. | |

FOREIGN PATENT DOCUMENTS

| CA | 2 356 614 A1 | 4/2000 |
| CA | 02483935 | 11/2004 |
| CA | 2 612 295 A1 | 1/2007 |
| CA | 2612295 A1 | 1/2007 |
| DE | 10 2004 060 146 A1 | 8/2004 |
| DE | 103 42 058 A1 | 4/2005 |

* cited by examiner

*Primary Examiner* — Nicholas Lucchesi
*Assistant Examiner* — Leah Stohr
(74) *Attorney, Agent, or Firm* — R. S. Lombard; K. Bach

(57) ABSTRACT

A single-use injector is disclosed comprising a housing (10), arranged in which are at least one mechanical spring energy store (50), at least one piston-cylinder unit (100), which can be effectively filled at least for a certain time, at least one piston-actuating ram (60) and at least one triggering unit (80). The spring energy store comprises at least one pre-tensioned spring element. The spring-loaded piston-actuating ram (60) has at least one retaining rod or hook (62), which can be moved transversely, at least in certain regions, and by means of a supporting portion supports the tensioned spring energy store on at least one resting surface of the housing. When actuation occurs, the triggering unit (80) releases the supporting portion to allow it to move away from the resting surface.

8 Claims, 7 Drawing Sheets

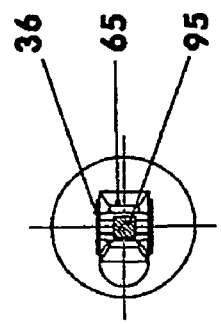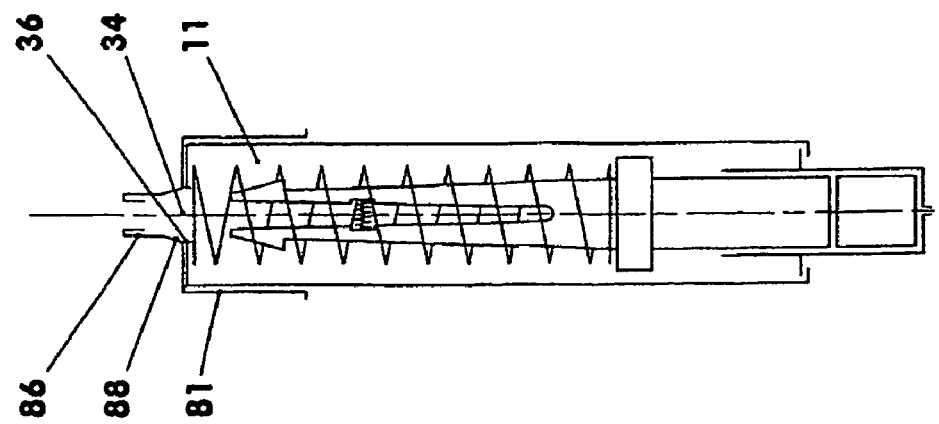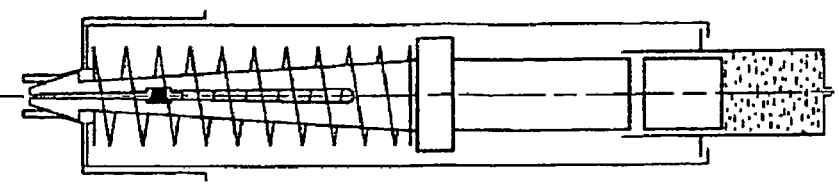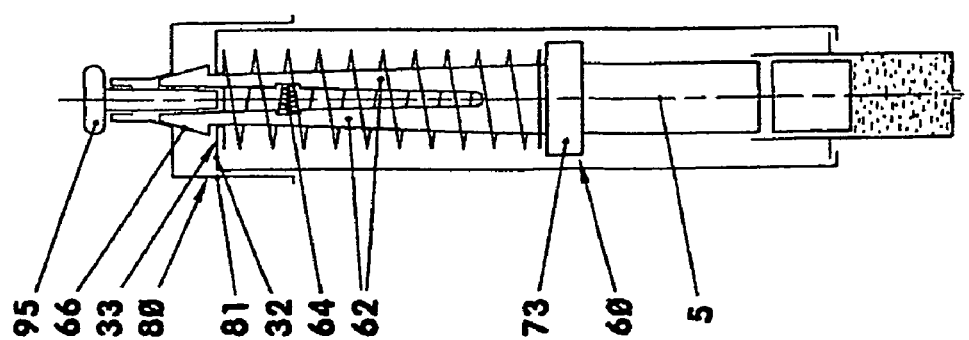

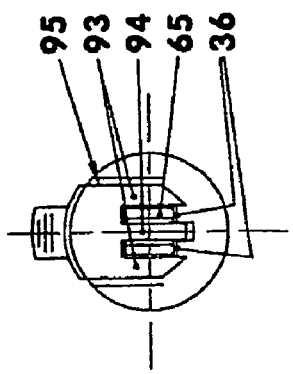
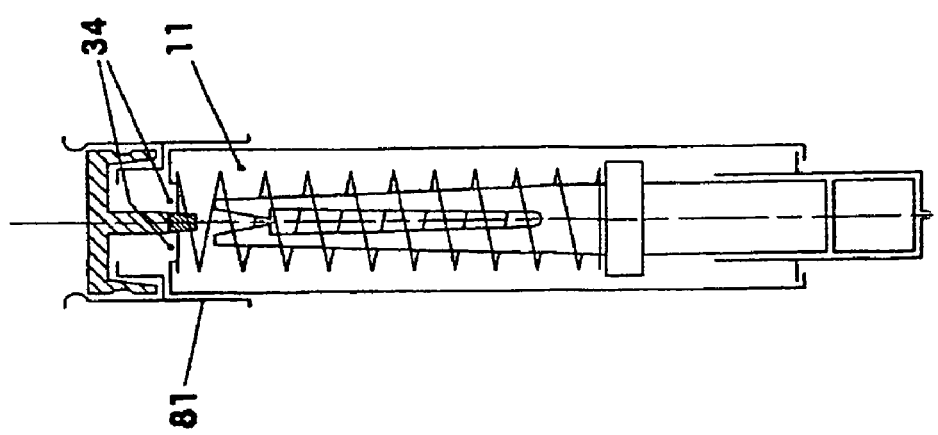
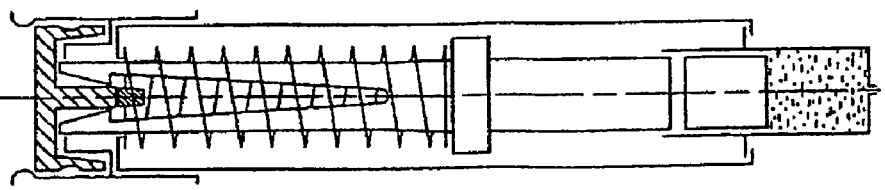
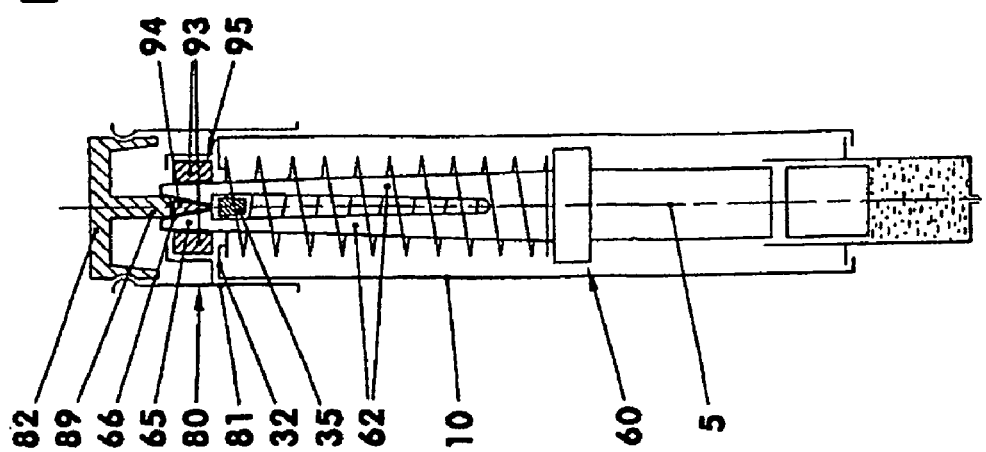

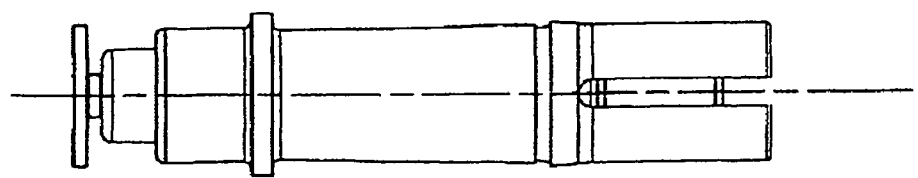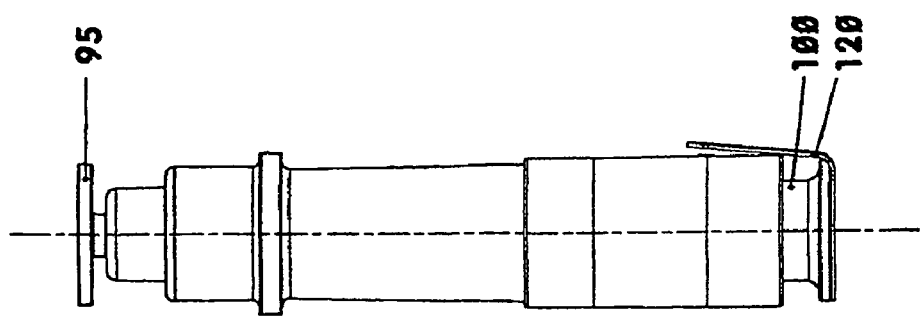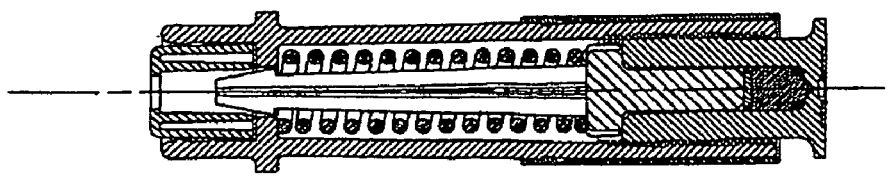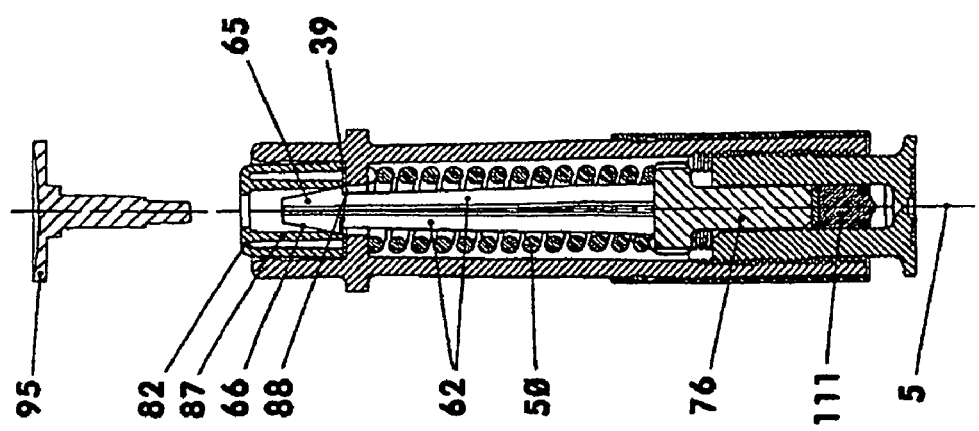

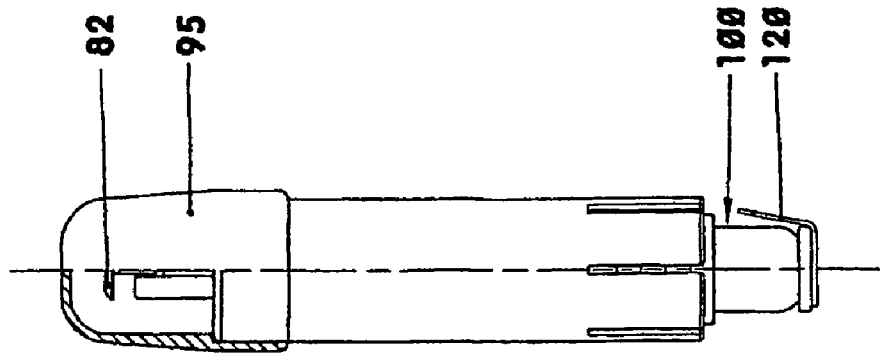
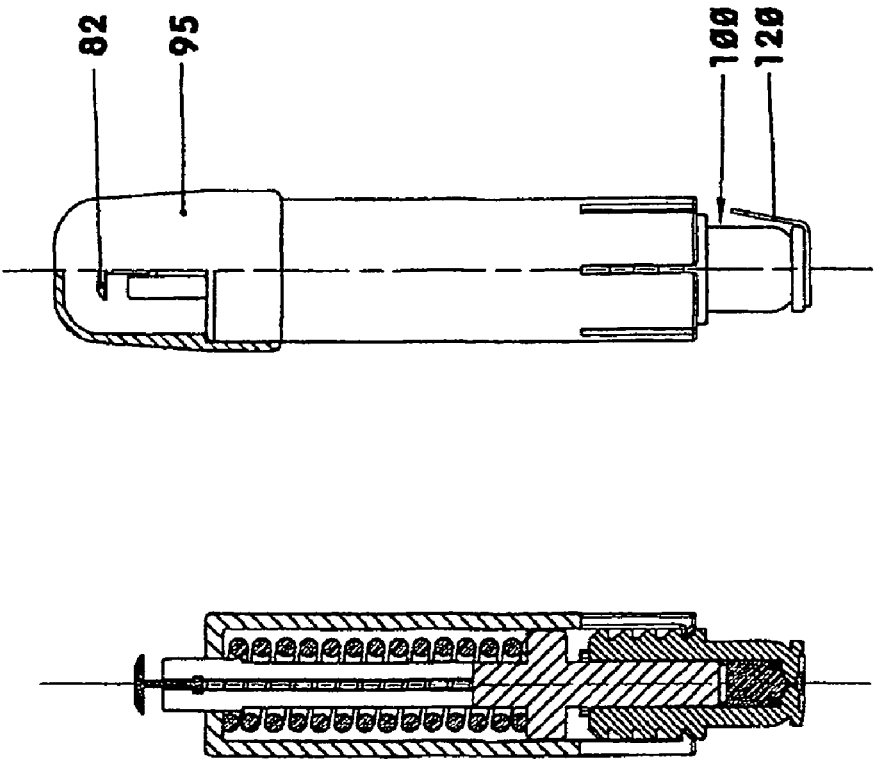
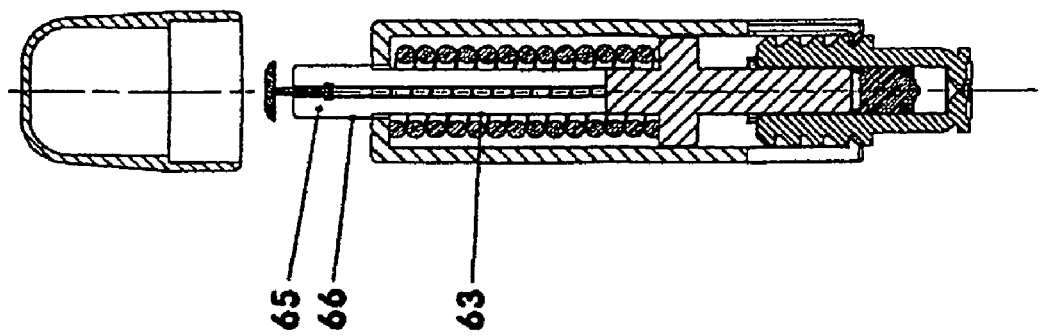

SINGLE-USE INJECTOR WITH AT LEAST ONE DRAW HOOK

CROSS-REFERENCE TO RELATED APPLICATION

This is a continuation-in-part application of pending international application PCT/EP 2008/000102 filed Jan. 9, 2008 and claiming the priority of German Application No. 10 2007 004 211.8 filed Jan. 27, 2007.

BACKGROUND OF THE INVENTION

The invention relates to a disposable injector with a housing in which or on which are arranged, in each case at least in some areas, at least one mechanical spring energy reservoir, at least one cylinder/piston unit that can be filled at least temporarily with active substance, at least one piston-actuating ram and at least one trigger unit, in which the spring energy reservoir comprises at least one pre-tensioned spring element and in which at least part of the piston-actuating ram is positioned between the spring energy reservoir and the piston of the cylinder/piston unit.

An injector of this kind, among other things, is known from EP 0 710 130 B1. It is constructed in such a way that the individual structural groups, namely the spring energy reservoir, cylinder/piston unit and trigger unit, cannot be separated from one another or handled separately. The trigger unit has a catch mechanism in which a slide that is moved transversely with respect to the centre line of the injector blocks or releases the piston-actuating ram via a notch or a thread groove.

DE 10 2004 060 146 A1 discloses an auto-injector for an automatic injection of an effective substance, comprising an elongated housing, an injection needle which is axially movably disposed in the housing and is connectable to an effective substance container, a piston which is movably disposed in the effective substance container for discharging the effective substance and a needle protection tube slidably disposed in the housing. A locking member is provided which, in a locking position, prevents movement of the effective substance container relative to the housing. However, the locking member can be brought, by displacement of the needle protection tube into the housing, into a release position in which movement of the effective substance container with respect to the housing is possible.

WO 03/092771 A1 discloses an injection device comprising:

a housing for accommodating a syringe which includes a bore in a front area, a needle which is in communication with the bore through the front area as well as a discharge or, respectively, dosing piston, which is movable in the bore relative to the front area in order to discharge the content of the syringe via the needle, wherein the housing has at one end thereof an opening through which the needle can extend;

a spring member, in order to pre-tension the syringe and the needle inwardly relative to the housing;

a drive element which is movable toward the one end for moving the needle of the syringe out of the opening and to move the discharge or, respectively, dosing piston of the syringe toward the front area;

a mechanism which is operable to release the syringe so that the needle moves inwardly with respect to the housing;

a drive coupling extending from the drive element to the discharge or, respectively, dosing piston of the syringe for transmitting a movement of the drive element to the discharge or, respectively dosing piston, wherein the drive coupling is longitudinally compressible.

When the drive element has moved the discharge or, respectively, dosing piston to the front, the drive coupling becomes slowly shorter and transmits a force sufficient to maintain the needle in its extended position while the discharge or, respectively, dosing piston is retained at the front until the mechanism releases the syringe.

Another design of an injection device with a needle and several corresponding syringes is known from WO 2007/002 052 A2.

The object of the present invention is therefore to develop a disposable injector of modular design which, with a small overall size, comprises only a small number of structural parts and, while being easy to handle, ensures safe storage and reliable operation.

SUMMARY OF THE INVENTION

The invention provides a single-use injector comprising a housing (10), arranged in which are at least one mechanical spring energy store (50), at least one piston-cylinder unit (100), which can be effectively filled at least for a certain time with an active substance, at least one piston-actuating ram (60) and at least one triggering unit (80). The spring energy store comprises at least one pre-tensioned spring element. The spring-loaded piston-actuating ram (60) has at least one retaining or draw hook (62), which can be moved transversely, at least in certain regions, and the retaining hook (62) by means of a supporting portion supports the tensioned spring energy store (50) on at least one resting surface of the housing. When actuation occurs, the triggering unit (80) releases the supporting portion of the retaining hook (62) to allow it to move away from the resting surface.

Accordingly, the spring-loaded piston-actuating ram (60) has at least one tension bar which is transversely movable at least in some areas and which, by means of a support portion, supports the tensioned spring energy reservoir on at least one bearing surface of the housing. The trigger unit is or has at least one trigger element which, when actuated, causes or enables a movement of the support portion away from the bearing surface.

With the invention, a needleless disposable injector is made available whose piston-actuating ram, upon triggering of the disposable injector, executes a movement that is oriented transversely with respect to the longitudinal direction and/or transversely with respect to the centre line of the disposable injector. For pre-tensioning and holding the spring energy reservoir, one or more parts of the piston-actuating ram bear with at least one enclosure or a hook on the housing or on a structural part arranged on the housing. If appropriate, it is also possible for only certain parts or areas of the piston-actuating ram to be designed to be movable relative to the housing of the disposable injector. To trigger the disposable injector, the enclosures or hooks are pushed down from their bearing surface on the housing, such that the piston-actuating ram, under the effect of the spring energy reservoir, can move at least approximately parallel to the centre line of the disposable injector.

BRIEF DESCRIPTION OF THE DRAWINGS

Further details of the invention will become clear from the following illustrative embodiments depicted schematically in the drawings, in which:

FIG. 4 shows schematically a disposable injector of the present invention with at least two oppositely disposed tension bars;

FIG. 5 shows the same as FIG. 4, but released and actuated;

FIG. 6 shows the same as FIG. 5, but after the medicament has been expelled;

FIG. 7 shows a plan view of the base of the disposable injector according to FIG. 4, but without the stepped trigger sleeve;

FIG. 8 shows schematically a disposable injector of the present invention with several tension bars, which have inwardly pointing tension hooks;

FIG. 9 shows the same as FIG. 8, but released and actuated;

FIG. 10 shows the same as FIG. 9, but after the medicament has been expelled;

FIG. 11 shows a plan view of the securing element of the disposable injector according to FIG. 8, but without the trigger element;

FIG. 13 shows the same as FIG. 12, but released and actuated;

FIG. 14 shows the same as FIG. 13, but after the medicament has been expelled;

FIG. 15 shows a side view of the disposable injector according to FIG. 12, before use;

FIG. 16 shows a side view of the disposable injector according to FIG. 12, but without the cylinder/piston unit and support sleeve;

FIG. 18 shows the same as FIG. 17, but released and actuated;

FIG. 19 shows the same as FIG. 18, but after the medicament has been expelled; and, FIG. 20 shows a side view of the disposable injector according to FIG. 17, but before use.

DETAILED DESCRIPTION OF THE PARTICULAR EMBODIMENTS

Figure 1:
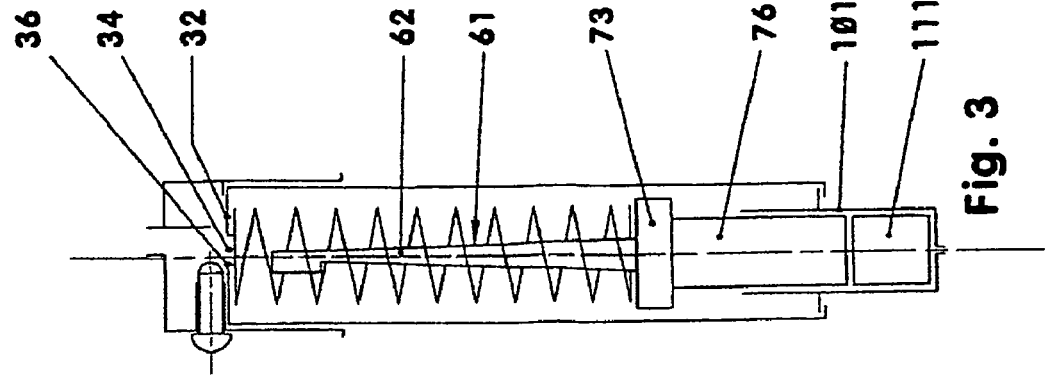
FIG. 1 shows schematically a disposable injector of the present invention with a tension bar.
Figure 2:
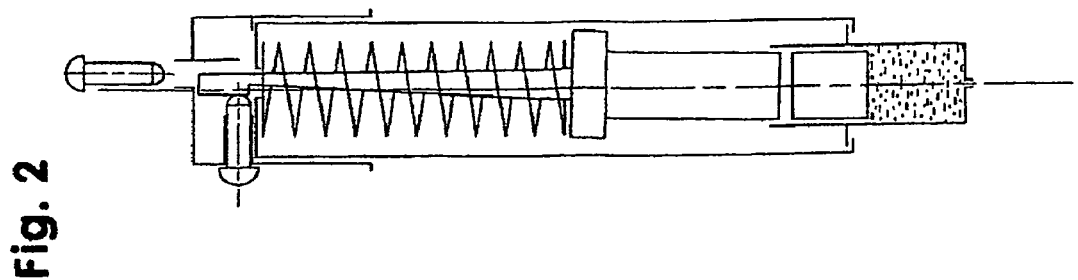
FIG. 2 shows the same as FIG. 1, but released and actuated.
Figure 3:
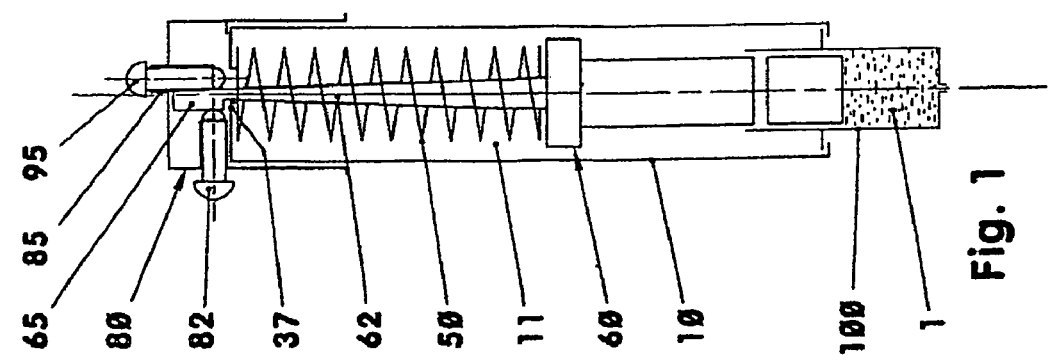
FIG. 3 shows the same as FIG. 2, but after the medicament has been expelled.

FIGS. 1 to 3 show the simplified principle of a disposable injector with a permanently charged spring energy reservoir. The disposable injector comprises a housing (10), a for example filled cylinder/piston unit (100), a piston-actuating ram (60) with tension-draw hooks or retaining hooks (62), and a helical compression spring (50) as spring reservoir. In addition, a trigger unit (80), in which a trigger element (82) and a securing element (95) are arranged, sits on the housing (10).

The housing (10) is a pot-shaped hollow body open at the bottom and with a base (32) lying at the top. The base (32) has, for example, an eccentric opening (34) through which, according to FIG. 1, the retaining hook (62) is engaged. The retaining hook (62) lies with its support portion (65) on the bearing surface (37) of the housing (10).

The piston-actuating ram (60) is divided into three areas. The lower area is the piston slide (76). Its diameter is slightly smaller than the internal diameter of the cylinder (101) of the cylinder/piston unit (100). The lower end face of the piston slide (76) acts directly on the piston (111).

The middle area is the ram plate (73). The ram plate (73) is a flat and in at least some areas cylindrical disc whose external diameter is a few tenths of a millimeter smaller than the internal diameter of the housing (10) in the jacket area (31). The upper area is the retaining hook (62).

The cylinder/piston unit (100) is secured in the lower part of the housing (10). The cylinder/piston unit (100) here consists of a cylinder (101) which is filled with an injection solution (1), such as a medicament, and in which a piston (111) lies in the rear position. Above the piston (111), the piston-actuating ram (60) is arranged in the housing (10) in such a way that, for example, although not touching the piston, it is laterally guided with its lower end in the upper area of the cylinder (101).

The helical compression spring (50) sits pre-tensioned between the ram plate (73) and the base (32) lying at the top of the housing (10).

The trigger unit (80) fits on the housing (10). In its for the most part closed end wall, it has a sleeve (85) in which a pin-shaped securing element (95) fits. The securing element (95) is positioned in combination with the housing (10) such that it holds the retaining hook (62) on the edge (36) of the opening (34) adjoined by the bearing surface (37). In the inserted state, the securing element (95) prevents accidental displacement of the tension hook (62) transverse to the longitudinal direction of the piston-actuating ram (60).

In the trigger unit (80), the trigger element (82) is mounted so as to be longitudinally displaceable transversely relative to the centre line (5) of the housing (10) for example. To actuate the disposable injector, the securing element (95) is pulled as in FIG. 2, the disposable injector is brought into position relative to the patient, and the trigger element (82) is then pressed, for example with a finger of the hand that is supporting the disposable injector. The trigger element (82) pushes the support portion (65) off from the support surface (37), with a slight tilting of the whole piston-actuating ram (60). The sliding movement takes place transverse to the longitudinal axis or centre line (5) of the disposable injector. Thereafter, the support portion (65), under the action of the helical compression spring (50), slips through the opening (34) into the interior (11) of the housing (10). In doing so, the cylinder/piston unit (100) is emptied, see FIG. 3.

In this principle, the piston slide (76) can also be designed as a separate structural part. For this purpose, it is then guided on the inside wall of the housing (10). It is also possible to form the piston slide (76) as a piston rod integrally on the piston (111) and thus to guide the piston rod only by the piston (111) and/or by a contact in some areas for example, on the inside wall of the cylinder (101). Of course, the piston slide (76) and the piston rod can share the space between the ram plate (73) and the piston (111) in any desired way.

The triggering operation is not restricted to the variant described here. Instead of the transversely displaceable trigger element (82), it is possible, for example, to use an eccentric gear, a screw gear or a lever gear.

FIGS. 4 to 6 show a refinement of the principle according to FIGS. 1 to 3. The piston-actuating ram (60) comprises, for example, two structurally identical retaining hooks (62) above the ram plate (73). Both retaining hooks (62) lie opposite each other in mirror symmetry. They are made, for example, of a resiliently elastic material. Both retaining hooks (62) lie back to back and seek to force themselves apart in the manner of a leaf spring, such that they bear on the edge (36) of the opening (34), for example with pre-tensioning. Their spring direction is symbolized in FIG. 4, for example, by a helical compression spring (64) lying transversely between them as an alternative.

Of course, such a helical compression spring (64) can also really be used if, for example, the tension hooks (62) are articulated on the ram plate (73) by means of pivot hinges.

The pivot axes of these pivot hinges would then lie transverse to the centre line (5) of the housing and perpendicular to the plane of the drawing according to FIGS. 4 to 6.

In this variant, as shown in FIG. 4, the support portions (65) via which the retaining hooks (62) bear on the for example plane outer face (33) of the base (32) have a wedge-shaped or frustoconical outer contour (66). Here, the cross section of the support portions (65) narrows upwards along the centre line (5). In FIGS. 4 to 6, the outer contours (66) are parts of pyramid surfaces that have a theoretical pyramid tip lying above the base (32) on the centre line (5), see FIGS. 4, 5 and 7.

A pin-shaped securing element (95) fits between the ends of the retaining hooks (62), see also FIG. 7. Here, it has a rectangular cross section, for example. The securing element (95), which is mounted for example in the housing (81) of the trigger unit (80), blocks the retaining hooks (62) mechanically in their locked position.

The trigger housing (81) has a pot-shaped design and sits longitudinally displaced on the rear part of the housing (10). A rectangular tube (86), for example, is mounted on the base of the trigger housing (81) and at the same time guides the securing element (95). At the transition from the base to the rectangular tube (86), the latter has bevelled areas (88). The bevelled areas (88) form the wedge surfaces on the trigger housing side.

After removal of the securing element (95), the trigger housing (81), like a press-button, can be moved downwards. In the process, the wedge surfaces (88) on the trigger housing side bear on the retaining hooks (62) and press these together, counter to the action of the symbolically indicated compression spring (64), such that the support portions (65) pass through the opening (34). The outer contour (66) of the support portions (65) and the wedge surfaces (88) on the trigger housing (81) side thus form a spline gear or slide wedge drive (66, 88). If appropriate, the wedge surfaces (88) and/or the surfaces of the wedge-shaped outer contour (66) of the support portions (65) can be curved with one or more axes, e.g. cylindrically or spherically, such that a curved surface slides along a plane surface or a surface of different curvature.

As soon as the for example elastically deformed retaining hooks (62), as parts of the piston-actuating ram (60), have reached the interior (11) of the housing (10), they spring back apart from each other.

With reference to FIGS. 8 to 11, a variant is described in which the tension hooks (62) lie facing each other, for example in pairs, i.e. the support portions (65) are directed towards each other. The tension hooks (62) in this case spring closed onto one another.

According to FIG. 8, the base (32) of the housing (10) in this variant has two for example rectangular recesses or openings (34), which are separated by a housing web or bar (35). The housing web (35), on which the support portions (65) of the retaining hooks (62) bear in the locked position of the disposable injector, is part of the housing base (32). In order to hold the hooks (62) securely on the housing web (35), they are partially enclosed above the housing base (32). For this purpose, a securing element (95) is used, see also FIG. 11. This securing element (95) is essentially a fork-shaped structural part with three prongs and a grip part that is guided in the trigger housing (81). The rear faces of the support portions (65) each bear on the outer prongs (93). The central prong (94) of the fork is located between the support portions (65) facing each other.

A trigger element (82) in the form of a press-button is also guided longitudinally in the trigger housing (81). A spreading rod (89) is formed integrally on the trigger element, for example centrally. According to FIG. 8, it bears on the central prong (94) of the securing element (95). The trigger element (82) is thus blocked until removal of the securing element (95).

To trigger the disposable injector, the securing element (95) is first of all pulled sideways completely out of the trigger housing (81). The press-button (82) is then depressed until it bears on the housing web (35), see FIG. 9. The spreading rod (89) and the wedge surface (66) interact in this process as a spline gear. The retaining hooks (62) are spread apart from each other, such that they can slide unimpeded through the openings (34) into the housing interior (11), see FIG. 10, in order to act there, as part of the piston-actuating ram (60), on the piston (111).

FIGS. 12 to 16 show an embodiment of the principle described in FIGS. 4 to 7. Here, the supporting structural part is the housing (10). It has a substantially tubular shape and is divided up into three functional areas (21, 31, 41). According to FIG. 12, the upper area is the trigger area (21). This is adjoined by the jacket area (31). An intermediate base (32) is arranged between the two areas and also protrudes slightly radially past the jacket area (31). The intermediate base (32) has a central recess or opening (34), the diameter of which widens slightly, for example towards the bottom.

In the trigger area (21) of the housing (10), a dimensionally rigid, for example metal, apertured disc (39) is located on the intermediate base (32). It is adhesively bonded or injection moulded therein. Instead of the apertured disc (39), it is also possible to use a ceramic reinforcement. The apertured disc (39) or the reinforcement protects the intermediate base (32) from pressures and/or other deformations. It also prevents sticking of the structural parts (32) and (65) that are otherwise in contact there.

The fixing area (41) for receiving the insertable cylinder/piston unit (100) is arranged below the jacket area (31). The fixing area (41) has for example three longitudinal slits, see FIG. 16. The inner wall of this area carries, for example, a trapezoidal thread (46). According to FIGS. 12 and 15, the fixing area (41) is enclosed by a support sleeve (49) that is locked on the housing (10).

A cylinder/piston unit (100) is screwed into the trapezoidal thread (46). Said unit consists of a cylinder (101) and a piston (111). The cylinder (101) is a thick-walled pot, for example, of which the cylindrical outer wall at least in some areas also carries a trapezoidal thread (104).

The rodless piston (111) sits in the for example cylindrical bore of the cylinder (101). At its front end face, of at least approximately conical configuration, the piston (111) has an axial annular groove (112) for receiving a sealing ring (114) or a permanently elastic sealing compound. A cylindrical metal plate (116) is let into the rear end face of the piston (111), for example.

A short cylindrical, nozzle-like bore (106) is located at the centre of the bore of the cylinder (101), whose cylinder base is adapted at least approximately to the contour of the front end face of the piston. The diameter of the bore (106) is approx. 0.1 to 0.5 millimeter. This bore (106) is one to five times as long as its diameter. It opens out in a cylindrical recess (107) of the outer end face (103) at the bottom of the cylinder (101).

The spring energy reservoir (50) or the drive unit of the disposable injector is arranged between the piston (111) and the trigger area (21). The spring energy reservoir (50) is a helical compression spring arranged on a piston-actuating ram (60) with four retaining hooks (62). By means of the support portions (65) of the retaining hooks (62), the helical compression spring (50) sits tensioned in the housing (10). It is supported between the inside face of the intermediate base (32) and an upper end face of the piston-actuating ram (60).

The piston-actuating ram (60) is divided into three areas. The lower area is the piston slide (76), the middle area is the ram plate (73) bearing the spring element (50), and the upper area is the bundle of for example four retaining hooks (62), see also the description of FIGS. 1 to 3.

In the jacket area (31) of the housing (10), the retaining hooks (62) have at least approximately a cylindrical envelope surface (63), i.e. their outer walls have the curvature of a cylinder jacket area. The support portion (65) has a frustoconical jacket as its envelope surface. The envelope surface is also designated as wedge contour (66).

The inner walls of the retaining hooks (62) are parts of an envelope surface (68) having the shape of a frustoconical jacket. This envelope surface (68) encloses the frustoconical jacket-shaped hollow space (67) located between the tension hooks. The cross sections of the hollow space (67) increase the further they are from the ram plate (73). The radial slits (69) lying between adjacent retaining hooks (62) increase in size towards the top, according to FIG. 12, to approximately twice the width.

Figure 12:
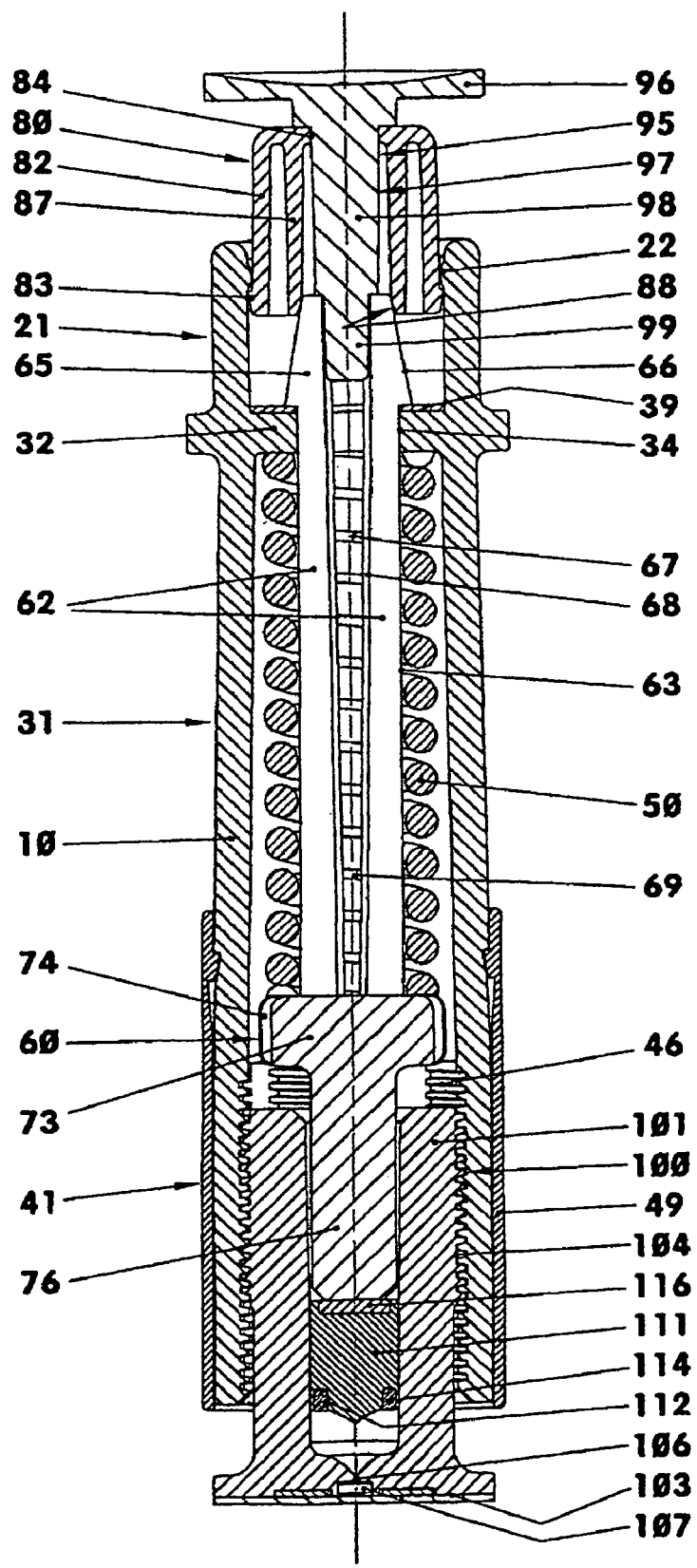
FIG. 12 shows a sectional view of the disposable injector, shown in FIG. 15, with several outwardly resilient retaining hooks.

In contrast to FIG. 1, the ram plate (73) according to FIG. 12 has for example two grooves (74) lying opposite each other.

The retaining hooks (62) lie with their support portions (65) in the trigger area (21). The support portions (65) lie secured on the apertured disc (39).

In the trigger area (21), a trigger unit (80) sits as a one-piece trigger element (82) in its upper position. The trigger element (82) is a pot-shaped body in whose interior a trigger tube (87) is integrally formed. At the lower end of the outer contour, the trigger element (82) has a peripheral, slightly protruding edge (83). The latter engages behind a peripheral bead (22) present on the inside wall of the trigger portion (21).

The base of the trigger element (82) has a circular recess or opening (84) in which a securing element (95) is inserted. The trigger tube (87) has a frustoconical wedge contour (88) at the lower end, in the area of the inside wall. In the illustrative embodiment, its cone angle is between 20 and 45 degrees. With the disposable injector in the unactuated and secured state, the wedge contour (88) bears in the upper area of the wedge contour (66) of the tension hooks (62).

The securing element (95) is, like the trigger element (82), a rotationally symmetrical structural part. It consists of a plate (96) and of a locking pin (97). The locking pin (97) has a locking area (99) and a support area (98). The two areas (98, 99) are frustoconical. They both have the same cone angle, for example. At least the cone angle of the locking area (99) corresponds to the cone angle of the hollow space (67). The support area (98) bears with its annular end face on the upper end faces of the tension or retaining hooks (62).

FIG. 13 shows the disposable injector with the securing element (95) removed and with the trigger element (82) actuated, i.e. pressed down. After the in this case vertical withdrawal of the securing element (95), the pressing down of the trigger element (82) causes the wedge contour (88) of the trigger tube (87) to slide along the wedge contours (66) of the tension hooks (62). In this process, the tension hooks (62) are bent elastically and/or plastically in the radial direction towards the centre line (5). The gap space between the individual tension hooks (62) is substantially used up at least in the area of the support portions (65). The maximum external diameters of the support portions (65) are now smaller than the diameter of the bore of the apertured disc (39). The tension hooks (62) can move downwards under the effect of the spring element (50) and displace the piston (111) by way of the piston slide (76), see FIG. 14.

FIG. 15 shows the as yet unactuated disposable injector. The securing element (95) is inserted, and the lower end face of the cylinder/piston unit (100) is sealed in a sterile manner by means of a tear-off adhesive seal (120).

FIGS. 17 to 20 show a disposable injector variant in which the retaining hooks (62) spring elastically towards the centre line (5) of the disposable injector. The housing (10) is essentially a smooth tube with a flat base (32) located at the top. A central bore (34) for passage of the piston-actuating ram (60) is formed in the base (32).

The fixing area (41) for receiving the insertable cylinder/piston unit (100) is located in the lower area of the housing (10). The fixing area (41) comprises for example six resilient hooks (42), which each end in an inwardly directed hook tip (43). Towards the lower end face (12) of the housing, the hook tips (43) have a bevel (44) that extends over the full thickness of the hook. The length and spring rate of the resilient hooks (42) is dimensioned such that the inserts (50, 100) required for the function of the disposable injector can be installed without plastic deformation of the resilient hooks (42).

One of these inserts is the cylinder/piston unit (100), see FIG. 6. It consists of a cylinder (101) and a piston (111), see also FIG. 12. The cylinder (101) is for example a thick-walled pot, of which the optionally cylindrical outer wall has for example five peripheral locking ribs (102). The sum of the locking ribs (102) has, in cross section, a saw tooth-shaped profile, for example, the division between the tooth-like locking ribs (102) being equidistant. The maximum diameter of the locking ribs (102) is slightly smaller than the internal diameter of the housing (10) in the fixing area (41). The diameter of the areas lying between adjacent locking ribs (102) corresponds to the minimum diameter of the housing (10) in the area of the hook tips (43).

The piston-actuating ram (60) sits between the base (32) and the cylinder/piston unit (100) in the housing (10). The two lower end areas (73, 76) of the piston-actuating ram (60) are known from FIG. 12. The upper area is formed by for example four retaining hooks (62), which for example do not reach as far as the ram plate (73). Between the ram plate (73) and the retaining hooks (62) there is a cylindrical portion (77) which, according to FIG. 17, serves among other things to guide the spring element (50). For this purpose, it has for example four short, radially protruding ribs, which fix the bottom winding of the spring element (50).

Each retaining hook (62) has a support portion (65). In the case of a triggered disposable injector, the bundle of retaining hooks (62) has a cylindrical envelope surface (63), see FIGS. 18 and 19. The envelope surface (66) can also be cylindrical in the area of the support portions (65).

In the upper area of the retaining hooks (62), each hook (62) includes a part of an annular groove (71) whose centre line is congruent with the centre line (5) of the disposable injector. According to FIG. 17, a for example cylindrical spreading disc (91) of a trigger element (82) sits in this annular groove (71). The bottom of the respective annular groove portions bears resiliently on the radial outer contour of the spreading disc (91). In the unloaded state, the retaining hooks (62) spring in the direction of the centre line (5). For example, on letting go the trigger element (82), they would touch at their upper ends.

Figure 17:
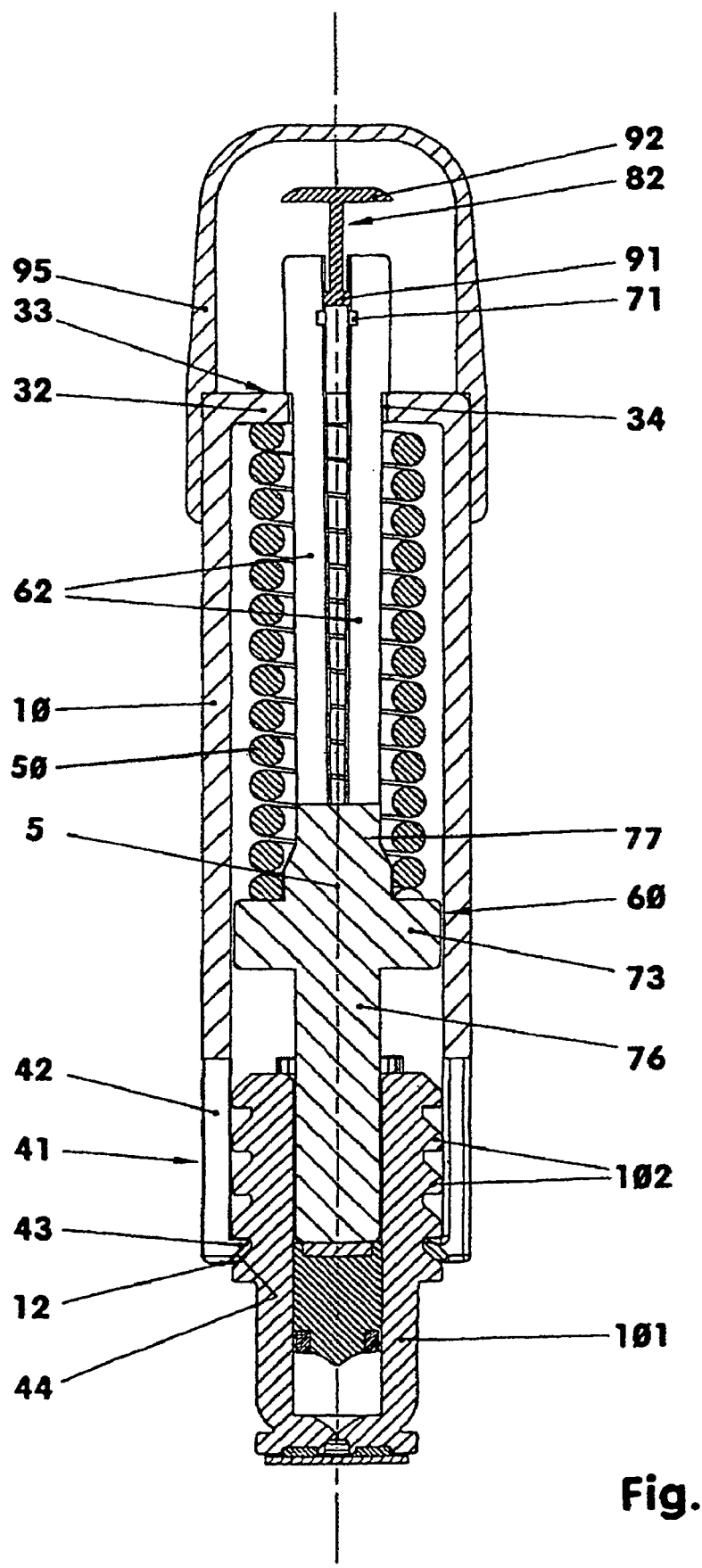
FIG. 17 shows a sectional view of a disposable injector, shown in FIG. 20, with several inwardly resilient tension bars.

The trigger element (82) shown in FIG. 17 has a mushroom shape as a rotationally symmetrical structural part. Trigger element (82) has a narrow web arranged for the spreading disc (91) and has at its upper end an integrally formed trigger disc (92).

To protect the trigger element (82), a securing element (95) in the form of a cap is fitted on the base (32) of the housing (10).

FIG. 20 shows this disposable injector in a side view, with the cap (95) shown in cross section on one side. The cylinder/piston unit (100) is closed with a tear-off protective film (120). According to FIG. 16, the trigger element (82) is in an upper position when the disposable injector is locked. The spreading disc (91) sits above the annular groove (71). The retaining hooks (62) adopt a spread-open position, with the support portions (65) bearing on the top (33) of the base (32).

If, after removal of the cap (95) and withdrawal of the protective film (120), the trigger element (82) is pressed into the piston-actuating ram (60), the spreading disc (91) of the trigger element (82) locks in the annular groove (71). The retaining hooks (62) spring back, such that the maximum external diameter of the envelope surface (66) of the support portions (65) is smaller than the diameter of the bore (34), see FIG. 18. The spring element (50) now drives the piston-actuating ram (60) downwards, see FIG. 19. With the delivery of the medicament via the cylinder/piston unit (100), the injection procedure is concluded.

Except for the spring elements (50, 64), all parts of the disposable injector are made of plastics or of materials similar to plastic or to rubber.

The following is a List of reference numbers:
1 injection solution; medicament
5 centre line of disposable injector
10 housing, in one piece
11 housing interior
12 housing end face, bottom
21 trigger area
22 bead
31 jacket area
32 base, intermediate base
33 outer face, end face, top
34 opening, bore, recess
35 web, housing web
36 housing edge
37 bearing surface
39 apertured disc
41 fixing area for the cylinder/piston unit
42 resilient hook
43 hook tip
44 bevel
46 trapezoidal thread
49 support sleeve
50 spring element, helical compression spring, spring energy reservoir
60 piston-actuating ram
61 tension bar
62 retaining hook, tension hook
63 envelope surface, bottom
64 helical compression spring, symbolic
65 support portion
66 outer contour, wedge-shaped; wedge surface; wedge contour; envelope surface, top
67 hollow space between the tension hooks
68 envelope surface of the hollow space
69 slits between the tension hooks
71 annular groove
73 ram plate
74 grooves
76 piston slide
77 cylindrical portion of piston-actuation ram
80 trigger unit
81 trigger housing, press-button
82 trigger element
83 edge
84 recess for securing element
85 sleeve
86 rectangular tube
87 trigger tube
88 wedge surfaces, areas, bevelled; wedge contour
89 spreading rod
91 spreading disc
92 trigger disc
93 outer prongs of (95)
94 middle prong of (95)
95 securing element, cap, fork
96 plate
97 locking pin
98 support area
99 locking area
100 cylinder/piston unit
101 cylinder
102 locking ribs, outside
103 end face
104 trapezoidal thread
106 bore, nozzle
107 recess in the end face
111 piston
112 annular groove
114 sealing ring, sealing means
116 metal plate
120 protective film, adhesive seal

What is claimed is:
1. A disposable injector comprising:
a housing (10) in which or on which are arranged, in each case at least in some areas, at least one mechanical spring energy reservoir (50), the housing (10) includes an intermediate base (32) having at least one bearing surface (37) or outer face (33) located proximate a housing edge (36),
at least one cylinder/piston unit (100) that can be filled at least temporarily with active substance,
a piston-actuating ram (60) and at least one trigger unit (80), the piston-actuating ram (60) includes a ram plate (73),
the spring energy reservoir (50) includes at least one pre-tensioned spring element, each of the at least one pre-tensioned spring elements rests on the ram plate (73) having a substantially flat upper surface,
at least part of the piston-actuating ram (60) is arranged in operative position between the spring energy reservoir (50) and a piston (111) of the cylinder/piston unit (100),
the ram plate (73) as a monolithic portion thereof includes at least two tension bars (61) the bottom of each tension bar (61) beginning directly from and as part of the substantially flat upper surface of the ram plate (73), the at least two tension bars (61) are transversely movable at least in some areas, support portions (65) operatively affixed to or a monolithic portion of the tension bars (61), the support portions (65) in a pre-actuated position are supported by the at least one bearing surface (37) or outer face (33) of the housing (10) proximate the housing edge (36), whereby the piston-actuating ram (60) is in supportive relationship with the tensioned spring energy reservoir (50) in the pre-actuated position,
the trigger unit (80) is or has at least one includes a trigger element (81, 82) positioned in operative arrangement with the support portions (65), the trigger unit (80) when actuated, for causing or for enabling a movement of the support portions (65) away from the bearing surface (37) or outer face (33) and the housing edge (36) of the housing (10), each tension bar (61) forms, together with one of the support portions (65), an outwardly resilient retaining hook (62), in the pre-actuated or locked position, engages over the housing edge (36), each retaining hook (62) has an inner wall which is part of an envelope surface (68) having the shape of a frustoconical jacket-shaped hollow space (67) located between the retaining hooks (62) enclosed by envelope surface (68), the frustoconical jacket-shaped hollow space (67) having cross-sections that increase the further the cross-sections are from the ram plate (73), the retaining hooks (62) adjacent to one another has radial slits (69) lying between adjacent retaining hooks (62), each radial slit (69) beginning at the upper flat surface of ram plate (73), each radial slits (69) increasing in size from the ram plate (73) toward the top of the adjacent retaining hooks (62).

2. The disposable injector according to claim 1, further including a securing element (95) arranged on the housing (10) or on the trigger unit (80), the securing element (95) for securing the retaining hooks (62) in a locked position before actuation of the trigger unit (80).

3. The disposable injector according to claim 1, wherein the trigger unit (80) further includes a slide wedge drive (66, 88) in mechanical communication with the piston-actuating ram (60).

4. The disposable injector according to claim 1, wherein each of the retaining hooks (62) has a length greater than half the length of the piston-actuating ram (60).

5. The disposable injector according to claim 1, wherein the piston-actuating ram (60) includes at least two resilient oppositely disposed retaining hooks (62), each having the support portions (65) of the retaining hooks (62) lie further apart from one another after actuation of the trigger unit (80).

6. The disposable injector according to claim 1, wherein the piston-actuating ram (60) includes at least two resilient oppositely disposed retaining hooks (62), each having the support portions (65) of the retaining hooks (62) lie closer together or touch one another after actuation of the trigger unit (80).

7. The disposable injector according to claim 1, wherein the base (32) has a central opening (34) passing therethrough, an apertured disc (39) is operatively affixed to the outer surface (33) of the base (32) in alignment with the central opening (34).

8. The disposable injector according to claim 7, wherein the apertured disc (39) comprises metal.

* * * * *